(12) United States Patent
Nishiyama et al.

(10) Patent No.: US 8,119,994 B2
(45) Date of Patent: *Feb. 21, 2012

(54) APPARATUS AND METHOD FOR INSPECTING SAMPLE

(75) Inventors: Hidetoshi Nishiyama, Tokyo (JP); Mitsuru Koizumi, Tokyo (JP)

(73) Assignee: JEOL Ltd., Tokyo (JP)

( * ) Notice: Subject to any disclaimer, the term of this patent is extended or adjusted under 35 U.S.C. 154(b) by 352 days.

This patent is subject to a terminal disclaimer.

(21) Appl. No.: 12/407,918

(22) Filed: Mar. 20, 2009

(65) Prior Publication Data

US 2009/0242762 A1    Oct. 1, 2009

(30) Foreign Application Priority Data

Mar. 26, 2008    (JP) .................................. 2008-080186

(51) Int. Cl.
   *H01J 37/20*    (2006.01)
(52) U.S. Cl. .................. 250/440.11; 250/310; 250/309
(58) Field of Classification Search .................. None
   See application file for complete search history.

(56) References Cited

U.S. PATENT DOCUMENTS

| | | | |
|---|---|---|---|
| 5,811,803 A * | 9/1998 | Komatsu et al. | 250/310 |
| 6,737,660 B2 * | 5/2004 | Miura et al. | 250/492.3 |
| 7,923,700 B2 * | 4/2011 | Nishiyama | 250/440.11 |
| 2004/0046120 A1 * | 3/2004 | Moses et al. | 250/311 |
| 2005/0173632 A1 * | 8/2005 | Behar et al. | 250/311 |
| 2009/0256074 A1 * | 10/2009 | Nishiyama | 250/306 |
| 2010/0051803 A1 * | 3/2010 | Koizumi et al. | 250/306 |
| 2010/0243888 A1 * | 9/2010 | Nishiyama et al. | 250/307 |

FOREIGN PATENT DOCUMENTS

| | | |
|---|---|---|
| JP | 47-24961 | 10/1972 |
| JP | 06-318445 | 11/1994 |
| JP | 2004-515049 | 5/2004 |
| JP | 2007-292702 | 11/2007 |
| JP | 2007292702 A * | 11/2007 |

OTHER PUBLICATIONS

Green, Evan Drake Harriman, Ph.D., "Atmospheric Scanning Electron Microscopy," Chapter 1: Introduction, Stanford University, 1993, pp. 1-12.

* cited by examiner

*Primary Examiner* — Jack Berman
*Assistant Examiner* — Michael Logie
(74) *Attorney, Agent, or Firm* — The Webb Law Firm

(57) ABSTRACT

Method and apparatus have a film including a first surface to hold the liquid sample thereon, a vacuum chamber for reducing the pressure of an ambient in contact with a second surface of the film, primary beam irradiation means connected with the vacuum chamber and irradiating the sample with a primary beam via the film, signal detection means for detecting a secondary signal produced from the sample in response to the beam irradiation, a partitioning plate for partially partitioning off the space between the film and the primary beam irradiation means in the vacuum chamber, and a vacuum gauge for detecting the pressure inside the vacuum chamber.

22 Claims, 6 Drawing Sheets

APPARATUS AND METHOD FOR INSPECTING SAMPLE

BACKGROUND OF THE INVENTION

1. Field of the Invention

The present invention relates to an apparatus and method capable of easily observing or inspecting a sample consisting of a liquid sample or cultured biological cells.

2. Description of Related Art

Living organisms, including we human beings, are multicellular animals. Living organisms develop diseases if information cannot be transmitted normally among cells or if viruses or chemical substances cling to cells. For this reason, in the fields of molecular biology and pharmaceutics, research is conducted by peeling off cells from a living organism, cultivating the cells on a laboratory dish, giving a stimulus, such as electricity, chemical substance, or medicine to the cells, and observing the resulting reaction on the cellular level.

In the past, optical microscopes have been used for such observation. Manipulators or pipettes have been employed to give stimuli to cells. Frequently, important portions to be observed are very tiny regions of less than 0.1 μm that are impossible to observe with an optical microscope. For example, diseases arising from the inability to exchange substances normally among biological cells include hypertension, diabetes insipidus, arrhythmia, myopathy, diabetes, and deprementia. Exchange of substances among cells is performed by ion channels having sizes of about 10 nm and existing in cell membranes. Because it is difficult to observe such ion channels with optical microscopes, there has been a demand for a technique enabling observation using a scanning electron microscope (SEM) having high resolution.

However, a sample to be inspected with an inspection apparatus incorporating SEM capabilities is normally placed in a sample chamber whose internal pressure has been reduced by vacuum pumping. The sample placed in the sample chamber, which, in turn, is placed in a reduced-pressure ambient in this way, is irradiated with an electron beam (charged-particle beam). Secondary signals, such as secondary electrons or backscattered electrons, produced from the sample in response to the irradiation are detected.

In such inspection of a sample using an SEM, the sample is exposed to a reduced-pressure ambient. Therefore, moisture evaporates from the sample, so that the cells die. It has been impossible to observe reactions of living cells to a stimulus.

Accordingly, when an inspection is performed under the condition where the sample contains moisture, it is necessary to prevent the sample from being exposed to the reduced-pressure ambient; otherwise, moisture would evaporate from the sample. One conceivable method of inspecting a sample using SEM without exposing the sample to a reduced-pressure ambient in this way consists of preparing a sample holder (sample capsule that may or may not be hermetically sealed) whose opening (aperture) has been sealed off by a film, placing the sample in the holder, and installing the holder in an SEM sample chamber that is placed in the reduced-pressure ambient.

The inside of the sample holder in which the sample is placed is not evacuated. The film that covers the opening formed in the sample holder (sample capsule) can withstand the pressure difference between the reduced-pressure ambient inside the SEM sample chamber and the ambient (e.g., atmospheric-pressure ambient) of the inside of the sample holder that is not pumped down. Furthermore, the film permits an electron beam to pass therethrough (see JP-T-2004-515049).

When a sample is inspected, a culture medium is first put into a sample capsule together with cells. The cells are cultivated on the film. Then, the sample capsule is placed into an SEM sample chamber that is in a reduced-pressure ambient. An electron beam is directed at the sample placed within the sample capsule from outside the capsule via the film on the capsule. Backscattered electrons are produced from the irradiated sample. The backscattered electrons pass through the film on the capsule and are detected by a backscattered electron detector mounted in the SEM sample chamber. Consequently, an SEM image is derived.

However, with this technique, the sample is sealed in the closed space and so it has been impossible to give a stimulus to cells or to manipulate them using a manipulator or pipette. The amount of the culture medium put into the sample capsule is about 15 μl. Therefore, as the culture medium evaporates, the salinity concentration rises, making it difficult to culture cells. Where the cells should be observed or inspected in vivo, there arises a problem.

This problem can be solved by increasing the size of the sample capsule to increase the capacity. However, if the film is damaged either by a stimulation induced by an electron beam or by a mechanical stimulus, a new problem is created. That is, the inside of the apparatus is contaminated with a large amount of culture medium.

An example of a method of obtaining an SEM image by preparing a film withstanding the pressure difference between vacuum and atmospheric pressure, irradiating a sample with an electron beam via the film, and detecting backscattered electrons produced from the sample in this way is described also in "Atmospheric scanning electron microscopy", Green, Evan Drake Harriman, Ph.D., Stanford University, 1993 (especially, Chapter 1: Introduction).

Examples in which two films of the structure described above are placed opposite to each other with a sample interposed between the films and in which an image is acquired by a transmission electron microscope are described in JP-A-47-24961 and JP-A-6-318445. Especially, JP-A-47-24961 also states a case in which an SEM image of the sample interposed between such films is acquired.

JP-A-2007-292702 discloses a sample inspection apparatus equipped with an open-close valve for partitioning the space between a film and a primary beam irradiation system within a vacuum chamber in order to permit the sample held on the film to be exchanged quickly and to prevent contamination of the inside of the vacuum chamber.

The resolution of an optical microscope is not high enough to observe very tiny regions of biological cells. Imaging using SEM is required. In order to observe cells by SEM while maintaining the liquid, a sample (cells) cultured on a laboratory dish is sealed into a sample capsule. The sample is irradiated with an electron beam via the film formed on the sample capsule. Thus, the sample is imaged.

However, the sample capsule is a narrow closed space. Therefore, there is the problem that it has been impossible to directly observe the state of the sample immediately after a stimulus is given from the outside to the sample using a manipulator or pipette. Furthermore, the capacity inside the sample capsule is small. Consequently, when moisture evaporates and the salinity concentration rises, it is difficult to culture cells for a long time inside the sample capsule. Hence, there are problems in observing cells for a long time.

In an attempt to solve this problem, the present invention is intended to provide an apparatus and method for inspecting a sample in such a way that biological cells held in a liquid state can be manipulated from the outside with a manipulator, pipette, or the like and that consideration is given to long-term observation.

JP-A-2007-292702 states that when a sample is exchanged, the space between the film and the primary beam irradiation means is partitioned off by the open-close valve and that under this condition, only the space on the film side is returned to the normal pressure. It also states that if the film is damaged during inspection of the sample, the valve is closed, partitioning off the space inside the vacuum chamber to thereby prevent contamination into the vacuum chamber.

With the open-close valve described in JP-A-2007-292702, however, the space inside the vacuum chamber is partitioned off hermetically. Therefore, it takes a considerable time to open and close the open-close valve. The portion that should be certainly prevented from being contaminated is the inside of the primary beam irradiation means (electron optical column). If it takes a considerable time to open and close the valve, it is not assured that contamination of the inside of the primary beam irradiation means is prevented.

SUMMARY OF THE INVENTION

The present invention relates to a sample inspection apparatus and method free of these problems. It is an object of the present invention to provide a sample inspection apparatus that can be easily maintained and serviced by preventing at least the inside of primary beam irradiation means from being contaminated. It is another object of the present invention to provide a sample inspection method implemented by the sample inspection apparatus.

A sample inspection apparatus, according to the present invention, has a film including a first film to hold a sample thereon, a vacuum chamber for reducing the pressure of an ambient in contact with a second surface of the film, primary beam irradiation column connected with the vacuum chamber and irradiating the sample with a primary beam via the film, signal detector for detecting a secondary signal produced from the sample in response to the beam irradiation, a partitioning member capable of partitioning off a region between the film and the primary beam irradiation column which are located opposite to each other, without hermetically isolating a side on which the film is located from a side on which the primary beam irradiation column is located within the vacuum chamber.

In one aspect of the present invention, there is further provided detector which, if there is any damage to the film, can detect the damage. When the damage to the film is detected, the partitioning plate can partition off the region. At the same time, the inside of the primary beam irradiation column and the inside of the vacuum chamber can be returned to the atmospheric pressure. In this case, gas can be supplied into the vacuum chamber via the inside of the primary beam irradiation column.

The partitioning plate may have a receiver dish structure capable of receiving and stopping the sample flowing into the vacuum chamber when the film is damaged. The first surface may hold the sample in an open state in which access to the surface from the outside is allowed. Furthermore, a manipulator having a front-end portion capable of being brought close to or making contact with the sample and optical image acquisition means for observing the sample and the manipulator may be provided.

Where there is the detector which, if there is any damage to the film, can detect the damage, the partitioning plate is automatically operated in response to the detection. The space inside the vacuum chamber is partially partitioned. The detector detects a rise in pressure inside the vacuum chamber caused by the damage to the film.

The first surface of the film may be the upper surface of the film. The second surface of the film may be the lower surface of the film. The primary beam is a beam of charged particles or an electron beam. The secondary signal can be at least one type of secondary electrons, backscattered electrons, X-rays, and cathodoluminescent light.

An inspection method, according to the present invention, starts with holding a sample on a first surface of a film. The pressure of a space in contact with a second surface of the film is reduced. The sample is irradiated with a primary beam via the film by primary beam irradiation column. A secondary signal produced from the sample in response to the beam irradiation is detected to inspect the sample. This method is characterized in that when any damage to the film is detected, a partitioning member partitions off a region between the film and the primary beam irradiation column which are located opposite to each other, without hermetically isolating a side on which the film is located from a side on which the primary beam irradiation column is located within the space.

In this method, when any damage to the film is detected, the partitioning plate can partition off the region. Concurrently, the inside of the primary beam irradiation column and the inside of the vacuum chamber can be returned to the atmospheric pressure. In this case, gas can be supplied into the vacuum chamber via the inside of the primary beam irradiation column.

The partitioning plate may have a receiver dish structure capable of stopping and accepting the sample. The first surface may hold the sample in an open state in which access to the surface from the outside is allowed. Furthermore, the sample may be manipulated. In addition, an optical image of the sample may be acquired.

The damage to the film can be detected based on a rise in pressure in the vacuum chamber caused by the damage to the film. The first surface of the film may be the upper surface of the film. The second surface of the film may be the lower surface of the film. The primary beam is a beam of charged particles or an electron beam. The secondary signal can be at least one type of secondary electrons, backscattered electrons, X-rays, and cathodoluminescent light.

In the sample inspection apparatus, according to the present invention, the partitioning plate partitions off the region across which the film and the primary beam irradiation column are located opposite to each other without hermetically isolating the side on which the film is located from the side on which the primary beam irradiation column is located within the vacuum chamber.

In the sample inspection method, according to the present invention, the partitioning plate partitions off the region across which the film and the primary beam irradiation column are located opposite to each other without hermetically isolating the side on which the film is located from the side on which the primary beam irradiation column is located in the space in contact with the second surface of the film.

Consequently, if the film is damaged and broken, and if the sample held on the film flows into the vacuum chamber (or the space), the partitioning plate quickly partitions off the region across which the film and primary beam irradiation column are located opposite to each other. Hence, contamination of at least the primary electron beam irradiation column can be prevented with certainty.

Accordingly, it is necessary to clean only the inside of the vacuum chamber. The sample inspection apparatus can be maintained and serviced easily. Additionally, damage to the primary electron beam irradiation means, which is expensive, can be prevented.

Other features and advantages of the present invention will become apparent from the following more detailed description, taken in conjunction with the accompanying drawings, which illustrate, by way of example, the principles of the present invention.

DESCRIPTION OF THE PREFERRED EMBODIMENTS

Sample inspection apparatus and method, according to the present invention, are hereinafter described with reference to the drawings.

Figure 1:
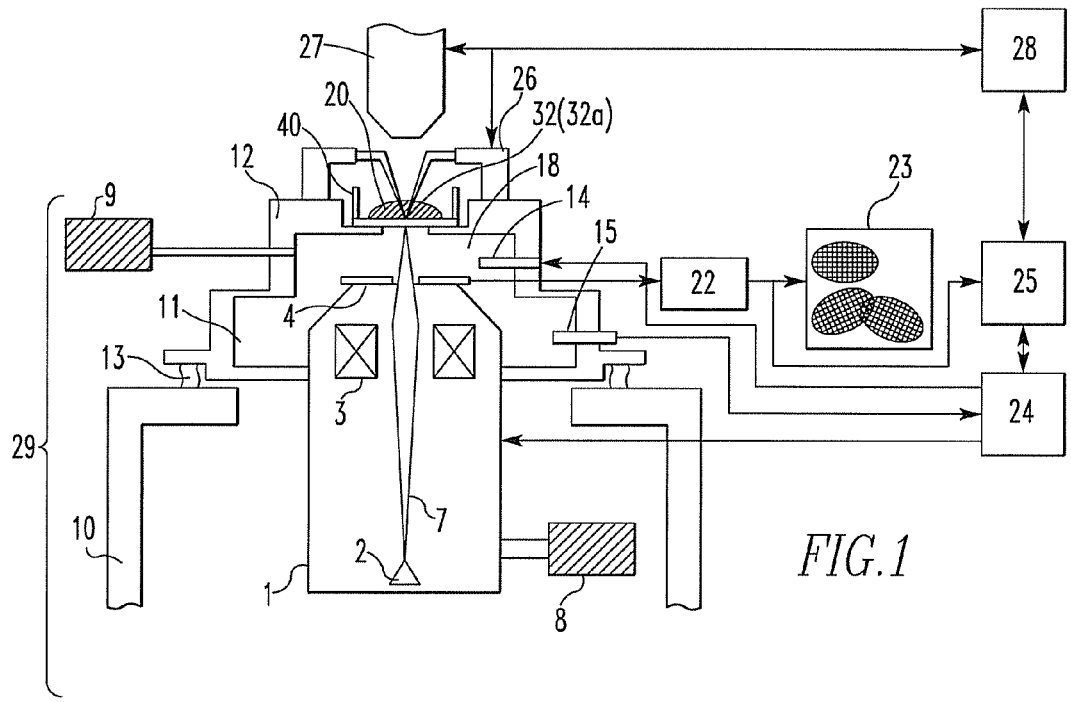
FIG. 1 is a schematic diagram of a first embodiment of the sample inspection apparatus, according to the present invention.

FIG. 1 is a schematic diagram of a first embodiment of the sample inspection apparatus, according to the present invention. The apparatus consists chiefly of an optical microscope 27, a manipulator 26, and an electron beam apparatus section 29 located under a sample holder 40. The electron beam apparatus section 29 includes an electron optical column 1 forming a primary beam irradiation column. An electron gun 2 forming an electron source is disposed in the electron optical column 1 and emits an accelerated electron beam 7 that is a primary beam. The electron beam 7 is one kind of charged particle beam. The beam 7 is focused by a condenser lens (objective lens) 3.

The focused electron beam 7 is directed at a liquid sample 20 via a sample-holding film 32 (described later) formed on the sample holder 40. The liquid sample 20 is held on the sample holder 40. In the present embodiment, the liquid sample 20 includes biological cells and a culture medium. The upper side of the sample 20 is open and in contact with a normal-pressure (atmospheric-pressure) ambient.

The front-end side of the electron optical column 1 is connected with a vacuum chamber 11. The electron gun 2 is mounted in the base side of the optical column 1. The base side of the column 1 is located under the vacuum chamber 11. Because of this configuration, the electron beam 7 released from the electron gun 2 travels upward through the optical column 1, passes through the space inside the vacuum chamber 11 and through the sample-holding film 32, and reaches the liquid sample 20.

During the irradiation, the electron beam 7 is deflected by deflection means (not shown). Thus, the beam 7 scans the liquid sample 20. At this time, a specimen contained in the liquid sample 20 is also scanned with the beam 7.

The electron optical column 1 forms the primary beam irradiation means in this way. In the present embodiment, the column is of the inverted type. A backscattered electron detector 4 is mounted on the front-end side of the optical column 1 inside the vacuum chamber 11. The backscattered electron detector 4 detects backscattered electrons produced when the specimen included in the liquid sample 20 is irradiated with the electron beam 7. For example, a semiconductor detector using a PN junction or a scintillator detector using a YAG crystal is used as the backscattered electron detector 4.

The output signal from the backscattered electron detector 4 is sent to an image formation device 22 disposed outside the vacuum chamber 11. The image formation device 22 forms image data based on the output signal from the detector 4. The image data corresponds to an SEM image, and is sent to a display device 23. The display device 23 displays an image based on the image data sent in. The displayed image forms an SEM image. If necessary, the image data formed by the image formation device 22 is sent to a computer 25. The computer 25 image-processes the image data and makes decisions based on the result of the image processing.

The inside of the electron optical column 1 is pumped down to a desired pressure by vacuum pump 8. The inside of the vacuum chamber 11 is evacuated to a desired pressure by vacuum pump 9. The vacuum chamber 11 is placed over a pedestal 10 via a vibration-proofing device 13.

A sample holder placement portion 12 is formed on top of the vacuum chamber 11 and provided with a hole to permit the electron beam 7 to be directed at the sample-holding film 32. The sample holder 40 is placed on the placement portion 12 via an O-ring (not shown). Consequently, the sample holder 40 is withdrawably supported in the vacuum chamber 11.

Figure 2:
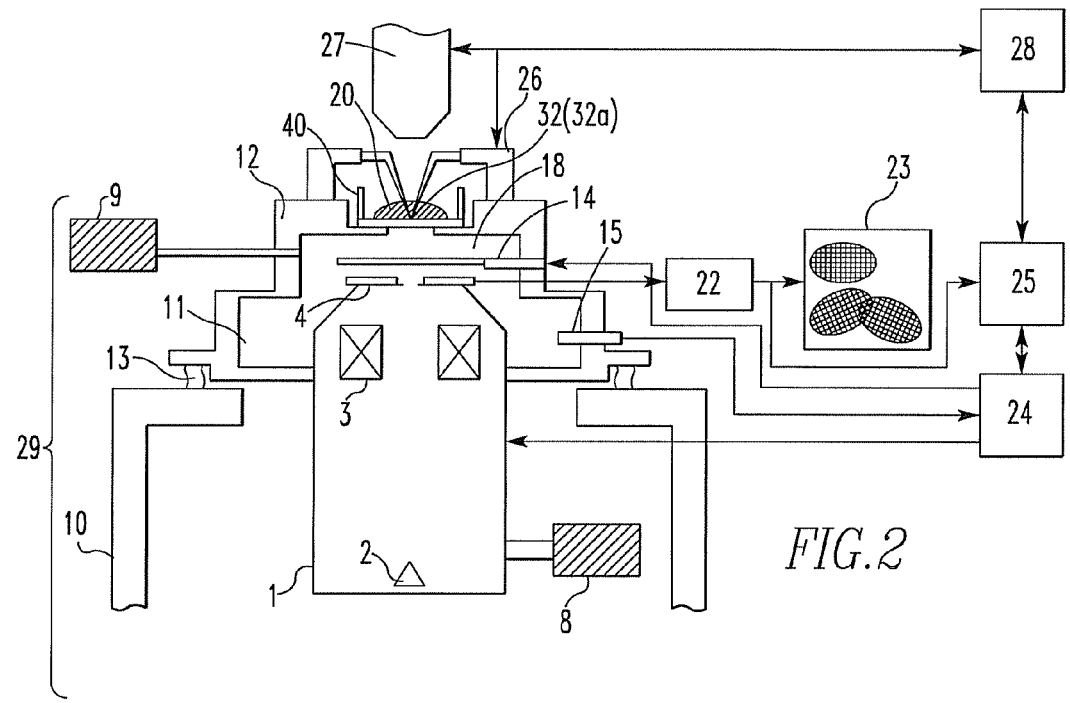
FIG. 2 is a schematic diagram similar to FIG. 1, but showing a different state.

A vacuum gauge 15 for detecting the pressure inside the vacuum chamber 11 is mounted in the vacuum chamber 11. A partitioning plate or partitioning member 14 is mounted between the front end of the electron optical column 1 and the sample-holding film 32. In FIG. 1, the partitioning plate 14 is in its open state. If the film 32 is damaged and the vacuum gauge 15 has detected a given rise in the pressure, the partitioning plate 14 automatically moves as shown in FIG. 2. For example, if the film 32 is damaged, the liquid sample 20 flows into the vacuum chamber 11, and the pressure inside the vacuum chamber increases above 100 Pa, then the partitioning plate 14 is moved as shown in FIG. 2.

After the partitioning plate 14 has been moved, it partitions off the region across which the sample-holding film 32 and the electron optical column 1 are disposed opposite to each other. Inside the sample chamber, the side on which the sample-holding film 32 is located is not hermetically isolated from the side on which the electron optical column 1 is located.

Consequently, the liquid sample 20 entered in the vacuum chamber 11 can be received and stopped by the partitioning plate 20, thus preventing contamination of the electron optical column 1 and backscattered electron detector 4. If the partitioning plate 14 is equipped with a receiver dish that receives liquid sample, then it is possible to cope with inflow of a large amount of liquid sample.

The partitioning plate 14 vertically partitions the inside of the vacuum chamber 11 into two spaces not completely but partially in this way. Therefore, the structure is simple. The partitioning plate can be operated at high speed. In the present embodiment, the partitioning plate can be set into operation (brought to the state of FIG. 2 from the state of FIG. 1) after a lapse of 0.1 second since the vacuum gauge 15 detected a rise in pressure. Furthermore, the partitioning plate can be thinned. Consequently, the distance between the front end of the electron optical column 1 and the sample-holding film 32 (i.e., the working distance of the SEM) can be reduced, thus achieving high resolution.

The electron beam apparatus section 29 having the electron optical column 1, vacuum chamber 11, partitioning plate 14, and vacuum gauge 15 is controlled by an electron beam controller 24. The manipulator 26 for giving a stimulus (such as a voltage, chemical substance, or medicine) to the sample and for moving it if necessary and an optical microscope 27 are placed on the sample holder placement portion 12. The microscope 27 permits one to observe the sample and to check the position of the manipulator 26. These components are controlled by an overall controller 28.

The optical axis of the optical microscope 27 is coincident with the optical axis of the electron beam 7. Alternatively, the center of field of view of the optical microscope 27 is coincident with the center of field of view of the SEM image. A region observed by the optical microscope can be made substantially coincident with the SEM image. The field of view of the SEM image and the field of view of the optical microscope 27 can be adjusted by manipulating the manipulator 26 or moving the sample holder placement portion 12 on which the sample holder 40 is placed by means of a moving mechanism (not shown).

The inspection apparatus, according to the present invention, has the electron beam apparatus section 29, manipulator 26, optical microscope 27, electron beam controller 24, overall controller 28, image formation device 22, and display device 23. These portions are connected with the computer 25. Information can be exchanged between these portions.

Figure 3:
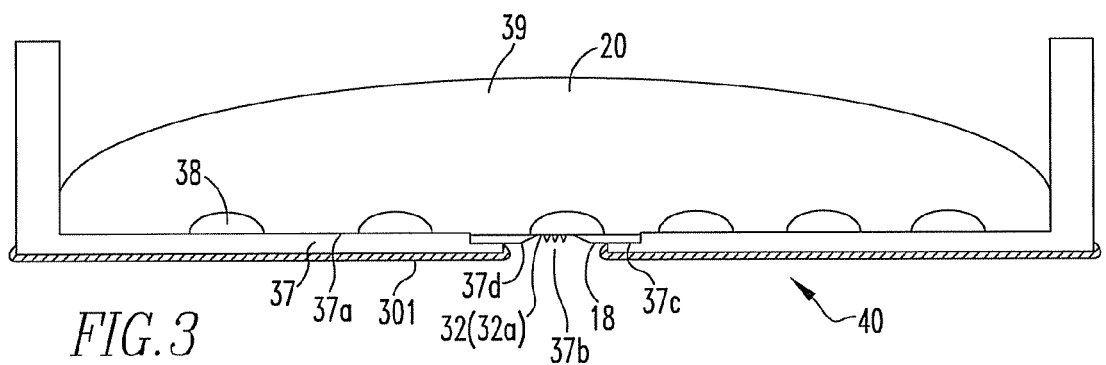
FIG. 3 is a cross-sectional view of a sample holder, according to the present invention.

The sample holder 40 is constructed as shown in FIG. 3. The sample holder 40 is composed of a dish-like body portion 37 made of plastic or glass and a film holder (frame-like member) 18 on which the sample-holding film 32 is formed. The film 32 transmits the electron beam 7. A recessed portion is formed inside the disk-like body portion 37. The bottom surface of the recessed portion forms a sample-holding surface 37a that is open.

The sample-holding surface 37a of the body portion 37 is (centrally in the example of FIG. 3) provided with a through-hole 37b. A step portion 37c is formed around the through-hole 37b on the side of the sample-holding surface 37a. The film holder 18 (frame-like member) is disposed on the step portion 37c and has the sample-holding film 32. The sample-holding film 32 has a first surface 32a that forms the sample-holding surface 37a. The sample-holding surface 37a is substantially flush with the sample-holding surface 37a of the body portion 37. Consequently, at least a part of the sample-holding surface 37a of the sample holder 40 is formed by the sample-holding film 32.

Tapering portions 37d are formed on the side of the through-hole 37b on the opposite side of the sample-holding surface 37a. The tapering portions 37d are spread apart toward the surface on the opposite side of the sample-holding surface 37a. The spread angle is set to 90° to 120°.

A region of the lower surface of the sample holder 40 might be exposed to a vacuum ambient and become irradiated with the electron beam 7. A conductive film 301 is formed on this region to prevent charging of the sample holder 40 when it is irradiated with the beam 7. The conductive film 301 is in contact with the film holder 18 (frame-like member). Electric charge accumulated by being irradiated by the electron beam 7 can be dissipated away to the liquid sample 20 via the film holder 18 (frame-like member) made of silicon. The presence of the conductive film 301 reduces the charging of the lower surface of the sample holder 40 and can prevent displacement of the orbit of the beam 7 (that would normally be produced when the liquid sample 20 is illuminated with the beam 7) and distortion and illumination spots in the SEM image that would be normally produced by displacement of the orbit of backscattered electrons.

Accumulation of electric charge can be prevented with certainty by connecting a grounding line to the liquid sample 20 or electrically connecting the conductive film 301 with the sample holder placement portion 12. The conductive film 301 can be formed, for example, by vapor-depositing aluminum or gold or applying silver paste.

Figure 4:
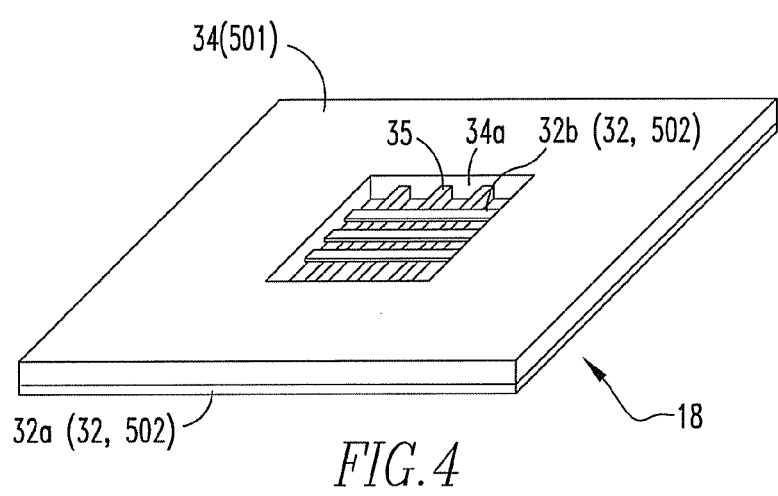
FIG. 4 is a schematic perspective view of a frame-like member constituting the sample holder, according to the present invention.

The structure of the film holder (frame-like member) 18 is shown in FIG. 4. The sample-holding film 32 is formed on a silicon substrate 34. The first surface 32a of the sample-holding film 32 (lower surface as viewed in FIG. 4; upper surface as viewed in FIG. 3) is exposed. The liquid sample 20 containing liquid, such as a culture medium, and sample cells is placed on the first surface (sample-holding surface) 32a of the sample-holding film 32. Since the first surface 32a is under atmospheric pressure, evaporation of moisture from the liquid sample 20 can be suppressed to a minimum.

The silicon substrate 34 is centrally provided with an opening 34a (upper surface in FIG. 4; lower surface in FIGS. 1 and 3) covered with the sample-holding film 32. A central portion of the second surface 32b of the sample-holding film 32 is exposed to the inside ambient of the vacuum chamber 11 through the opening 34a. The first surface 32a of the sample-holding film 32 is exposed to the atmospheric-pressure ambient, while the second surface 32b is exposed to the vacuum ambient. In order to withstand the pressure difference, the film 32 is supported and reinforced with a lattice 35.

Figure 5:
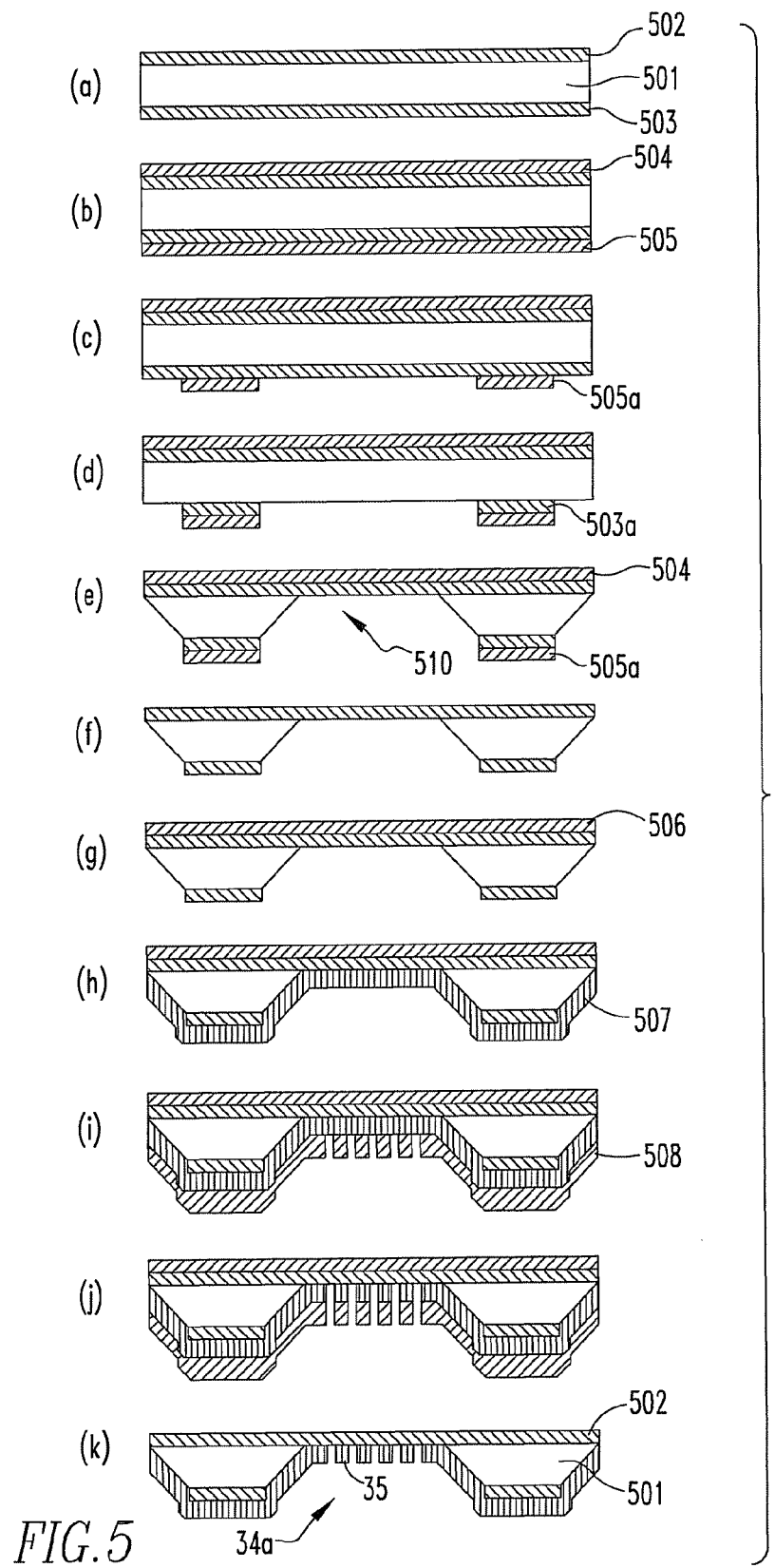
FIG. 5 shows cross sections illustrating a method of fabricating the frame-like member constituting the sample holder, according to the present invention.

A method of creating the film holder (frame-like member) 18 is next described by referring to FIG. 5. First, as shown FIG. 5(a), silicon nitride films 502 and 503 are formed on a silicon substrate 501 using CVD (chemical vapor deposition). A typical thickness of the films 502 and 503 is 30 nm. Layers of resist 504 and 505 are applied on the silicon nitride films 502 and 503, respectively (FIG. 5(b)). The layer of resist 505 is patterned photolithographically to leave behind resist layer portions 505a (FIG. 5(c)). Using the resist pattern as a mask, the silicon nitride film 503 is processed by dry etching, and silicon nitride film portions 503a are left behind (FIG. 5(d)).

Using the pattern as a mask, the silicon substrate 501 is wet-etched with KOH to form an opening 510 (FIG. 5(e)). The resist layer portions 504 and 505a are removed by ashing (FIG. 5(f)). Where the lattice 35 is not present, the film holder (frame-like member) 18 is completed at this point. Resist 506 is applied on the layer of silicon nitride film 502 (FIG. 5(g)). A layer of metal 507 of Al or Ni is formed to a thickness of 1 μm on the opposite side of the silicon nitride film 502 (FIG. 5(h)). Resist layer 508 is applied on the metal layer 507, and a pattern is photolithographically formed using a mask (FIG. 5(i)). Using the resist layer 508 as a mask, the metal layer 507 is etched (FIG. 5(j)). Finally, the resist layer 508 is removed by ashing or organic cleaning (FIG. 5(k)). As a result, the opening 34a and lattice 35 are formed.

The film holder (frame-like member) 18 fabricated in this way is inverted up and down from the state of FIG. 4. The first surface 32a of the silicon nitride film 502 that is the sample-holding film 32 is taken as an upper surface. The second surface 32b can also be taken as an upper surface.

The film holder (frame-like member) 18 is firmly attached to the step portion 37c over the through-hole 37b formed in the dish-like body portion 37 forming the sample holder 40. Thus, the sample holder 40 is fabricated (FIG. 3). To attach the holder (frame-like member) 18 to the step portion firmly, bonding using an epoxy-based or silicone-based adhesive or fusion making use of heat, ultrasonic waves, or laser light can be used. Consequently, the film holder (frame-like holder) 18 is firmly held in a position corresponding to the through-hole 37b in the sample-holding surface 37a of the body portion 37.

In the present embodiment, the body portion 37 and film holder (frame-like member) 18 are combined to fabricate the sample holder 40. The sample-holding film 32 may be directly firmly bonded to the body portion 37. The body portion 37 and the sample-holding film 32 may be fabricated integrally. Furthermore, cell adhesion molecules (described later) acting as molecules for bonding the sample may be applied to the sample-holding surface 37a including the first surface 32a of the sample-holding film 32.

The thickness of the silicon nitride film 502 is set to a range of from 10 to 1,000 nm. The sample-holding film 32 of the film holder (frame-like member) 18 is made of silicon nitride. In addition, the film 32 may be made of silicon oxide, boron nitride, polymer, polyethylene, polyimide, polypropylene, or carbon. Where films of these materials are used, their film thicknesses are set to a range of from 10 to 1,000 nm. The sample-holding film 32 made of the aforementioned material transmits the electron beam 7 but does not transmit gas or liquid. Moreover, it is necessary that the film be capable of withstanding a pressure difference of at least 1 atmosphere across the opposite surfaces.

As the thickness of the sample-holding film 32 is reduced, scattering of the electron beam 7 is reduced and, therefore, the resolution is improved but the film is more easily damaged. As the thickness is increased, scattering of the electron beam 7 increases, resulting in decreased resolution. However, the film is less likely to be damaged. The preferable thickness of the film is 20 to 200 nm.

A sample inspection method, according to the present invention, is next described. First, as shown in FIG. 3, cells 38 forming a sample are cultured within a culture medium 39 using the sample holder 40. In order to culture the cells 38 in this way, it is necessary to graft the sample cells from the laboratory dish where they have been previously cultured to the sample holder 40. For this purpose, a normal method as described below is used.

The culture medium is Product No. D5796 of Sigma-Aldrich Co., for example. First, the culture medium is discarded from the laboratory dish where the cells have been previously cultured. A mixture liquid of trypsin and EDTA (ethylenediaminetetraacetic acid) is put into the dish to peel off the cells adsorbed to the dish. The peeled cells are recovered into a centrifuge tube. A culture medium is put into the tube. The trypsin is inactivated and then the cells are spun down. Then, the supernatant fluid is discarded from the centrifuge tube and the remaining liquid is stirred in the culture medium. A part (e.g., 1/10) of the stirred liquid including the cells 38 is entered into the sample holder 40. The culture medium (liquid sample) 39 is grafted.

Under this condition, the holder is allowed to stand still in a cell culture chamber. After a lapse of several hours, the cells 38 begin to be adsorbed onto the sample-holding surface 37a of the sample holder 40 including the first surface 32a of the sample-holding film 32 and proliferate. The aforementioned method may be modified according to cells, and is merely one example. Consequently, the cells 38 which are to be observed or inspected and become a sample are cultured within the sample holder 40. It follows that the liquid sample 20 containing the cultured cells 38 and culture medium 39 is constituted.

Depending on biological cells, if cell adhesion molecules (molecules for bonding of the sample) are applied to the sample-holding surface 37a of the sample holder 40 (especially, the first surface (sample-holding surface) 32a of the sample-holding film 32 observed with an electron beam), cultivation is facilitated. The cell adhesion molecules cause cells arranged for cultivation and cells proliferated by cultivation to be adsorbed onto the sample-holding surface. Examples of the cell adhesion molecules include collagen, fibronectin, vitronetin, cadherin, integrin, claudins, desmogleins, neuroligin, neurexin, selectin, laminins, and poly-L-lysine.

After the cells are cultured within the sample holder 40 as described above, the sample holder 40 is placed on the holder placement portion 12. At this time, the partitioning plate 14 is closed and in the state of FIG. 2. Subsequently, the insides of the vacuum chamber 11 and electron optical column 1 are evacuated to desired degrees of vacuum using the vacuum pumps 8 and 9. For example, the pressure inside of the electron optical column 1 is set below 1 Pa. The pressure inside the electron optical column 1 (especially, around the electron gun 2) is set to about $10^{-4}$ to $10^{-5}$ Pa, for example.

The positions of the cells 38 and of the manipulator 26 are then checked with the optical microscope 27. A glass microtube holding microelectrodes therein is installed at the front end of the manipulator. A voltage can be applied to the cells through the microelectrodes. A liquid can be made to flow in and out through the glass microtube for manipulation.

Under this condition, the manipulator 26 is moved while making an observation with the optical microscope 27 to bring the cells 38 close to the glass microtube. Then, a negative pressure is applied to the glass microtube to bring it into intimate contact with the cell membranes. As a result, potential response can be measured.

When the manipulator 26 is moved as described above, if the sample-holding film 32 is erroneously damaged or destroyed, and if the liquid sample 20 flows into the vacuum chamber 11, the liquid sample 20 can be received and stopped by the partitioning plate 14 because the plate is closed. Consequently, the electron optical column 1 is not contaminated. Where the partitioning plate 14 is not present as in the prior art, the liquid sample 20 enters the electron optical column 1, making it necessary to clean or replace the column. As a result, the apparatus is made usable.

We now return to the observation sequence. After checking that the sample-holding film 32 on which the liquid sample 20 is placed has not been damaged, the partitioning plate 14 is opened. Thus, the inside of the vacuum chamber 11 is ceased to be partitioned. Thereafter, in order to prevent light from entering the backscattered electron detector 4 via the sample-holding film 32, the light illumination of the optical microscope 27 is ceased. Other extraneous light is blocked in a manner not shown. The blocking also shields the film holder (frame-like member) 18 and liquid sample 20 against radiation rays produced when the electron beam 7 hits the film holder (frame-like member) 18 and sample 20.

Then, as shown in FIG. 1, the electron beam 7 is directed at the liquid sample 20 including the cells 38 from the electron optical column 1 to perform imaging. The beam 7 passes through the sample-holding film 32 of the sample holder 40 and hits the cells 38. Backscattered electrons produced from the cells 38 in response to the illumination are detected by the backscattered electron detector 4.

Since the aforementioned tapering portions 37d are formed around the through-hole 37b of the dish-like body portion 37 forming the sample holder 40, collision of the backscattered electrons against the inner side surface of the through-hole 37b can be suppressed to a minimum. That is, the backscattered electrons can be suppressed from being blocked. The backscattered electrons can be detected efficiently by the backscattered electron detector 4.

A detection signal produced from the backscattered electron detector 4 is fed to the image formation device 22, which, in turn, forms image data based on the detection signal. Based on the image data, an image (SEM image) is displayed on the display device 23.

Subsequently, an electrical stimulus is given to the cells 38 using the microelectrodes installed at the front end of the manipulator 26 to manipulate the cells. An SEM image is acquired in the same way as in the above-described process step. The response of the cells 38 to the stimulus is checked.

After the imaging, the partitioning plate 14 is closed to prevent contamination of the electron optical column 1 if the sample-holding film 32 should be damaged. Before a variation caused by application of a stimulus to the cells 38 is observed by SEM as described above, an observation may be made with the optical microscope 27. Also, at this time, if the partitioning plate 14 is closed, risk of contamination occurring when the sample-holding film 32 is broken can be reduced.

In any case, if the partitioning plate 14 is closed when the electron beam 7 is not directed at the liquid sample 20, the probability of contamination of the inside of the apparatus can be reduced by shortening the interval for which the partitioning plate 14 is opened during inspection.

Where the speed of reaction of the cells 38 to the stimulus is low, the partitioning plate 14 may be once closed. The plate 14 may be again opened at a time when a reaction is deemed to have taken place. Then, imaging may be performed using the electron beam 7. The reaction can be checked with the optical microscope 27.

The manipulator 26 can have a mechanism capable of spraying a chemical substance or medicine into the liquid sample 20. Behavior of the cells 38 in response to the chemical substance or medicine can be observed or inspected while observing the cells by SEM. Furthermore, a function of permitting a liquid to flow out can be imparted to the manipulator 26. This permits the sprayed substance to be recovered. Also, the pH of the culture medium and the osmotic pressure can be maintained constant.

In the foregoing, backscattered electrons are used to form an image. Backscattered electrons produce a signal intensity proportional to the atomic number. Therefore, where the sample is almost totally made of substances of low atomic numbers, such as a biological sample, the image contrast is very low, and it is difficult to improve the resolution.

Accordingly, a heavy metal, such as gold, may be adsorbed onto portions of the cells 38 to be noticed in their behavior. In particular, gold is adsorbed onto the portions (antigen) via an antibody by causing the antigen tagged with gold particles having the nature of being adsorbed on the portions (antigen) to be sprayed against the cells by making use of an antigen-antibody reaction. Furthermore, a fluorescent dye or quantum dots (e.g., nanoparticles of Si or particles of CdSe coated with ZnS and having sizes of 10 to 20 nm) that emit light when irradiated with an electron beam may be previously adsorbed onto certain portions of the cells 38, and the emitted light may be observed with an optical microscope.

In the above embodiment, normally used gold particles have particle diameters of 10 to 30 nm. However, the adsorptive force between the antibody and gold particles is weak, and gold particles of 10 to 30 nm may not be attached. In this case, very small gold particles (nanogold particles) having particle diameters of the order of nanometers are first attached to the antibody. Under this condition, the gold particles are too small and it is difficult to observe them by SEM. Silver is adsorbed around the gold particles by making use of a silver sensitizer. This makes it easier to detect them by SEM.

In the foregoing, cells previously cultured in a laboratory dish are taken out and grafted onto the sample holder 40. Then, the cells are cultured. Alternatively, cells may be taken from a living organism and directly placed on the sample-holding surface 37a of the sample holder 40. The cells may be cultured in the sample holder 40.

As described so far, the present invention makes it possible to observe a specimen by SEM via the sample-holding film 32, the specimen being included in a liquid. Especially, the use of an open sample chamber facilitates giving a stimulus to (or manipulating) cells using the manipulator because access to the sample can be made from the outside.

During observation with the SEM under the condition where the partitioning plate 14 is opened as shown in FIG. 1, if the sample-holding film 32 is broken, the liquid sample 20 flows into the vacuum chamber 11, increasing the pressure. If the vacuum gauge 15 has detected the increased pressure to be higher than 100 Pa, for example, information about it is sent to the electron beam controller 24, and an instruction for closing the partitioning plate 14 is sent to the partitioning plate 14.

As a result, the partitioning plate 14 is moved as shown in FIG. 2. The liquid sample 20 is received and stopped by the partitioning plate 14. Where the amount of the liquid sample 20 is large, it is possible to prepare a receiver dish on the partitioning plate 14. It takes only 0.1 second until the partitioning plate 14 is closed after detection of a pressure rise. The contamination of the electron optical column 1 can be reduced to a level at which no cleaning is necessary. In this way, the present invention enhances convenience in use of the apparatus. Furthermore, the amount of culture medium can be increased. Cells are allowed to survive for a long time. SEM imaging can be performed for a long time.

In the present invention, the inverted type SEM is used. Depending on samples, a normal non-inverted type SEM using a sealed sample capsule as described in the "Description of the Related Art" of this specification can be used without problem. In this case, also, the partitioning plate 14 needs to be located between the sealed sample capsule and the front end of the electron optical column 1.

In the above embodiments, an electron beam is used as the primary beam. If the sample-holding film 32 shows sufficient shock resistance and strength against impingement of other charged-particle beams, such as a helium ion beam, the present invention can also be applied in a case where the other charged-particle beam is used.

In the above embodiments, backscattered electrons are used as a secondary signal. Information about the cells 38 can also be obtained by detecting other forms of information, such as secondary electrons, X-rays, cathodoluminescent light, and electric current absorbed into the cells 38 forming a sample. It is convenient to use the manipulator 26 in measuring the absorption current.

It is required that the sample-holding film 32 of the present embodiment withstand a pressure difference of at least 1 atm. and that gas or liquid do not flow in or out. Specifically, the material of the film 32 includes at least one of polymer, polyethylene, polyimide, polypropylene, carbon, silicon oxide, silicon nitride, and boron nitride.

Figure 6:
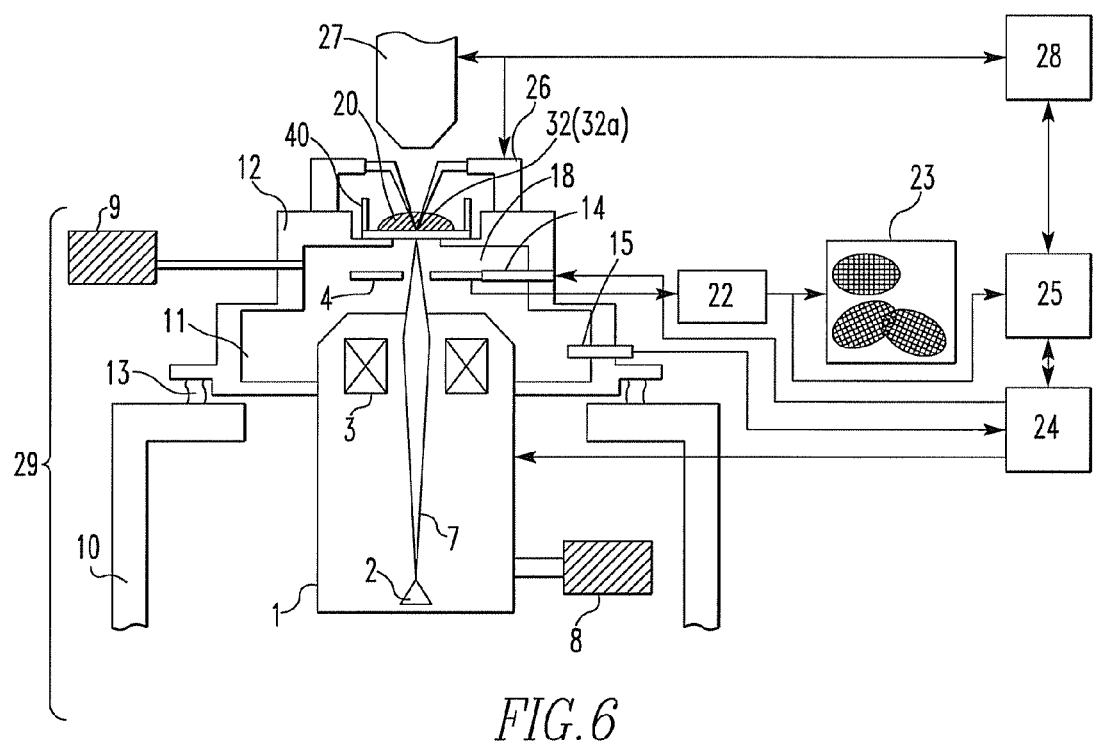
FIG. 6 is a schematic diagram of a modification of the first embodiment of the sample inspection apparatus, according to the present invention.

In the above embodiments, the partitioning plate 14 and backscattered electron detector 4 are fabricated separately. As a modified embodiment, they may be integrated as shown in FIG. 6. That is, in the embodiment of FIG. 6, the backscattered electron detector 4 is mounted at the front end of the partitioning plate 14. In this structure, when the partitioning plate 14 is opened, the backscattered electron detector 4 is located immediately above the electron optical column 1, maximizing the efficiency at which backscattered electrons are detected.

Figure 7:
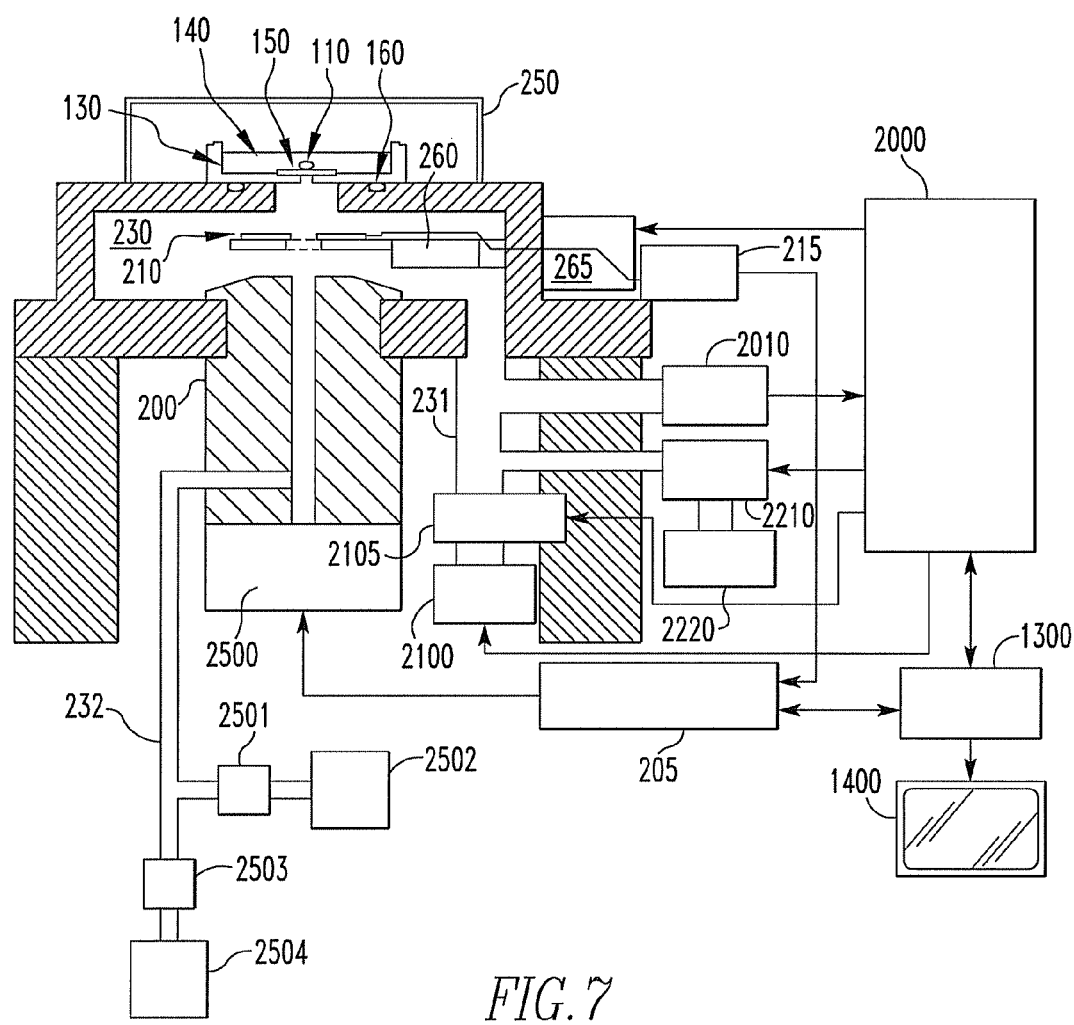
FIG. 7 is a schematic diagram of a second embodiment of the sample inspection apparatus, according to the present invention.

A second embodiment of the sample inspection apparatus of the present invention is next described by referring to FIG. 7. The sample inspection apparatus shown in FIG. 7 inspects a sample by irradiating cells 110 held on a sample-holding film 150 with an electron beam from below via the film 150.

The sample-holding film 150 is held in a laboratory dish 130. A sample 140 consisting of a liquid culture medium and the cells 110 is held in the dish 130. Under this condition, the dish 130 is placed over a vacuum chamber 230 via an O-ring 160. An opening is formed in an upper part of the vacuum chamber 230 and located opposite to the sample-holding film 150 in the laboratory dish 130.

The front end of an electron optical column 200 acting as primary beam irradiation means is connected with a lower part of the vacuum chamber 230. The column 200 is controlled by an SEM control circuit 205. Correspondingly, an electron beam is emitted from an electron gun 2500 disposed in the electron optical column 200 toward the sample 140.

When the electron beam is made to impinge on the cells 110 via the sample-holding film 150, backscattered electrons are produced from the cells 110 and detected by a backscattered electron detector 210. The output signal from the detector 210 based on the detected backscattered electrons is amplified by a preamplifier 215 and accepted into a control computer 1300 via the SEM control circuit 205.

A two-dimensional image based on a signal from the control computer 1300 is displayed as a sample image on a display monitor 1400. An X-ray shielding cover 250 is mounted to prevent X-rays produced from the vicinities of the sample in response to the electron beam irradiation from leaking from the apparatus. The ambients inside and outside the cover 250 are at normal pressure (atmospheric pressure).

The inside of the vacuum chamber 230 is evacuated via a tube 231 by a vacuum pump 2100. The tube 231 is connected with the bottom surface of the inside of the vacuum chamber 230 as shown. The pump 2100 is connected with the tube 231 via a valve 2105.

A pressure gauge 2010 acting as pressure detector is connected with the tube 231. A leaking gas supply source 2220 is connected also with the tube 231 via another valve 2210. The pressure gauge 2010 can detect the pressure inside the vacuum chamber 230 via the tube 231.

The pressure gauge 2010, vacuum pump 2100, and valves 2105, 2210 are controlled in operation by a vacuum control system 2000.

On the other hand, the inside of the electron optical column 200 is evacuated by a vacuum pump 2504 via a tube 232. The tube 232 is connected into the column 200 as shown. The pump 2504 is connected with the tube 232 via a valve 2503. A leaking gas supply source 2502 is connected with the tube 232 via a valve 2501. The vacuum pump 2504 and valves 2501, 2503 are also controlled in operation by the vacuum control system 2000.

The backscattered electron detector 210 is mounted at the front end of the partitioning plate or partitioning member 260. The partitioning plate 260 is driven by a partitioning plate driver 265, which, in turn, is controlled in operation by the vacuum control system 2000. The detector 210 is provided with an opening to permit passage of the electron beam coming from the electron optical column 200.

In the sample inspection apparatus constructed as described so far, when the cells 110 are observed or inspected, the insides of the vacuum chamber 230 and electron optical column 200 are pumped down to set degrees of vacuum.

Specifically, the vacuum control system 2000 closes the valve 2210 and opens the valve 2105. The inside of the vacuum chamber 230 is evacuated by the vacuum pump 2100 via the tube 231.

The vacuum control system 2000 closes the valve 2501 and opens the valve 2503. Consequently, the inside of the electron optical column 200 is evacuated by the vacuum pump 2504 via the tube 232.

Under this condition, an electron beam is directed at the cells 110 forming a sample from the electron gun 2500 in the electron optical column 200 through the vacuum chamber 230. The beam reaches the cells 110 through the sample-holding film 150. Backscattered electrons produced from the cells 110 at this time pass through the sample-holding film 150 and reach the backscattered electron detector 210, where the electrons are detected. As a result, a sample image is formed.

During the observation or inspection of the sample as described above, if the sample-holding film 150 holding the sample 140 including the liquid and cells 110 is damaged or destroyed, atmosphere enters through the damaged portion of the film. The degree of vacuum of the ambient inside the vacuum chamber 230 deteriorates. For example, when the inside pressure is set to 1 Pa, the pressure increases rapidly to above 30 Pa. In this case, the vacuum deterioration is detected by the pressure gauge 2010, and information about it is sent to the vacuum control system 2000.

When the information is detected, the vacuum control system 2000 operates the partitioning plate driver 265. Consequently, the partitioning plate 260 moves through the vacuum chamber 230 and is placed between the sample-holding film 150 and the electron optical column 200. At this time, the partitioning plate 260 partitions off the region across which the sample-holding film 150 and electron optical column 200 are located opposite to each other without hermetically isolating the side where the sample-holding film 150 is located from the side where the column 200 is located inside the vacuum chamber 230.

Consequently, the partitioning plate 260 can be instantly moved at high speed. If the sample-holding film 150 is damaged and the sample 140 including liquid intrudes into the vacuum chamber 230, most of the entering sample is received and stopped by the partitioning plate 260.

Simultaneously with the above-described operation, the vacuum control system 2000 closes the valve 2105 on the side of the tube 231 and the valve 2503 on the side of the tube 232 and opens the valve 2501 on the side of the tube 232. Consequently, vacuum pumping through the tube 231 is stopped. Also, vacuum pumping through the tube 232 is stopped. Leaking gas, such as nitrogen from the gas supply source 2502, is supplied into the electron optical column 200 via the tube 232.

The leaking gas supplied into the electron optical column 200 reaches the inside of the vacuum chamber 230. The inside of the column 200 and the inside of the vacuum chamber 230 including the inside of the tube 231 are returned to the atmospheric pressure. At this time, the leaking gas flows into the vacuum chamber 230 from inside the column 200 via the front end of the column 200 and so if the sample-holding film 150 is damaged and the sample 140 containing liquid enters the vacuum chamber 230, the sample 140 does not enter the column 200. Consequently, contamination is prevented.

Where it is desired to return the inside of the vacuum chamber 230 to the atmospheric pressure quickly, the leaking gas can also be supplied from the gas supply source 2220 into the vacuum chamber 230 via the tube 231 by opening the valve 2210 on the side of the tube 231. In this case, it is desired to set the flow rate of the leaking gas supplied from the gas supply source 2220 smaller as compared with the flow rate of the leaking gas supplied from the gas supply source 2502 into the column 200 because the flow of the leaking gas from inside the column 200 into the vacuum chamber 230 should be maintained.

In order to prevent the pressure inside the vacuum chamber 230 from becoming higher than the atmospheric pressure by the supply of the leaking gas (i.e., back pressure is created), the vacuum control system 2000 may close the valves 2501 and 2210 when the pressure gauge 2010 has detected that the pressure inside the vacuum chamber 230 has reached a pressure slightly lower than the atmospheric pressure.

In this way, a sample inspection apparatus, according to the present invention, has a sample-holding film (32, 150) including a first film on which a sample is held, a vacuum chamber (11, 230) for reducing the pressure of an ambient in contact with a second surface of the film, primary beam irradiation column (1, 200) connected with the vacuum chamber and irradiating the sample with a primary beam via the film, signal detector (4, 210) for detecting a secondary signal produced from the sample in response to the beam irradiation, a partitioning member (14, 260) capable of partitioning off a region across which the film and the primary beam irradiation column (1, 200) are located opposite to each other without hermetically isolating the side on which the film is located from the side on which the primary beam irradiation means (1, 200) is located inside the vacuum chamber.

The detection means (15, 2010) is provided which, if the film (32, 150) is damaged, detects the damage. When the detection means has detected the damaged to the film, the partitioning member (14, 260) can partition off the region.

Furthermore, there is provided the pressure restoration means (2220, 2502) which, when the detection means (15, 2010) has detected any damage to the film, returns the inside of the primary beam irradiation means (1, 200) and the inside of the vacuum chamber (11, 230) to the atmospheric pressure.

In this structure, when the detection means (15, 2010) has detected any damage to the film, the pressure restoration source (2502) supplies leaking gas into the vacuum chamber (230) via the inside of the primary beam irradiation means (200), whereby the insides of the primary beam irradiation means (200) and vacuum chamber (230) can be returned to the atmospheric pressure. The detection means (15, 2010) can detect any damage to the film based on a rise in pressure inside the vacuum chamber (11, 230).

The partitioning member (14, 260) can have a receiver dish structure.

The signal detector (4, 210) can be mounted to the partitioning member (14, 260).

The first surface of the sample-holding surface can hold a sample under an open state to permit a manipulator to make access to the surface from the outside. The apparatus can have the manipulator whose front end can be brought close to or make contact with the sample held on the first surface of the film and optical image acquisition means for observing the sample and the manipulator.

The first surface of the sample-holding film can be taken as the upper surface of the film, while the second surface of the film can be taken as the lower surface of the film. The primary beam released from the primary beam irradiation means (1, 200) can be a beam of charged particles or electron beam. The secondary signal can be at least one type of secondary electrons, backscattered electrons, X-rays, and cathodoluminescent light.

The sample inspection method, according to the present invention, can be implemented by inspecting a sample with the above-described sample inspection apparatus.

The sample inspection method, according to the present invention, starts with holding a sample on a first surface of a sample-holding film (32, 150). The pressure of a space in contact with a second surface of the film is reduced. The sample is irradiated with a primary beam via the film by primary beam irradiation means (1, 200). A secondary signal produced from the sample in response to the primary beam irradiation is detected, thus inspecting the sample. When any damage to the film is detected, the region across which the film and the primary beam irradiation means (1, 200) are located opposite to each other can be partitioned off by the partitioning member (14, 260) without hermetically isolating the side on which the film is located from the side on which the primary beam irradiation means (1, 200) is located inside the space.

When any damage to the film is detected, the inside of the primary beam irradiation means (1, 200) and the space can be returned to the atmospheric pressure. When any damage to the film is detected, the inside of the primary beam irradiation means (1, 200) and the space can be returned to the atmospheric pressure by supplying leaking gas into the space via the inside of the primary beam irradiation means (1, 200). The damage to the film can be detected based on a rise in pressure inside the space.

Additionally, the sample held on the first surface of the film can be manipulated. An optical image of the sample can be acquired.

Figure 8:
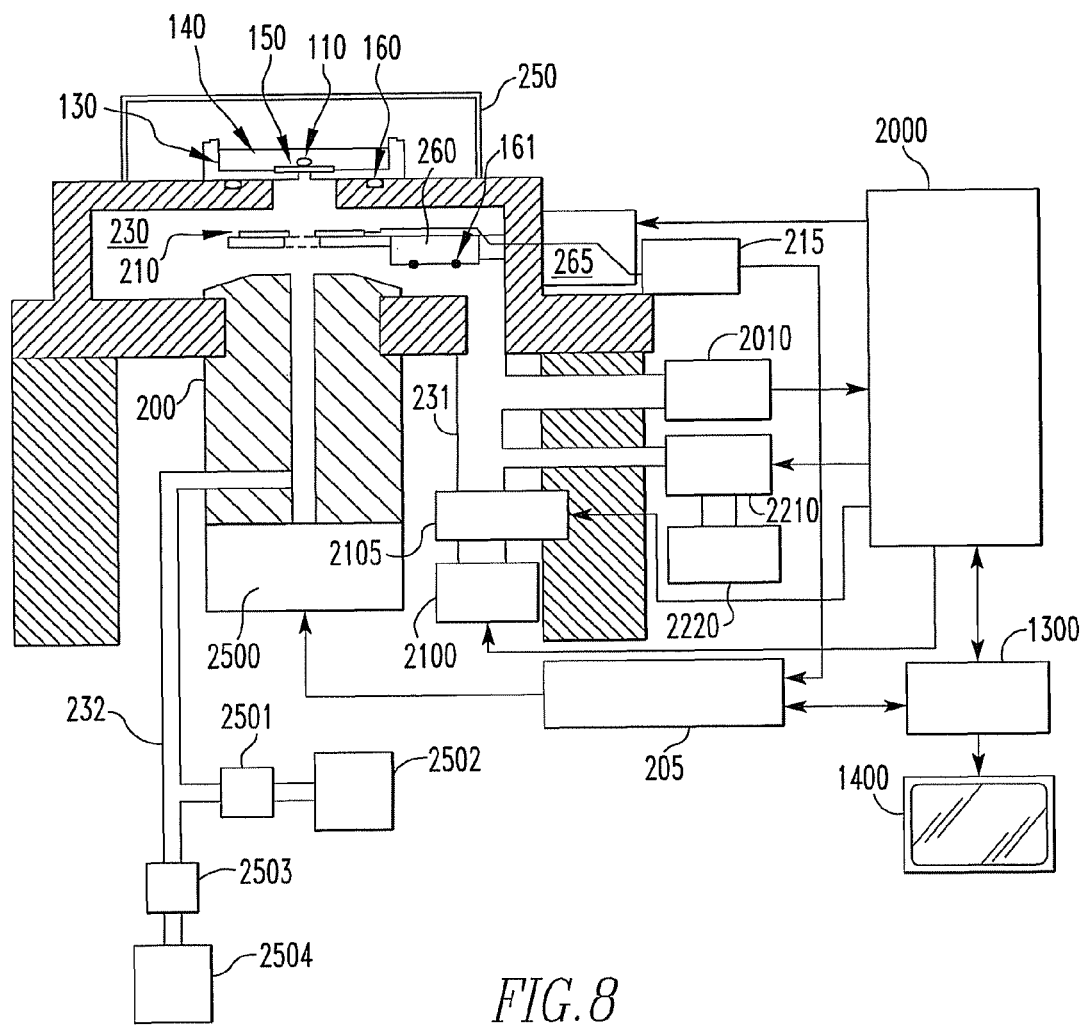
FIG. 8 is a schematic diagram of a modification of the second embodiment of the sample inspection apparatus, according to the present invention.

Finally, a modification of the second embodiment is shown in FIG. 8. The differences between the sample inspection apparatus shown in FIG. 8 and the apparatus shown in FIG. 7 are that the lower surface of the partitioning plate 260 is located slightly below the lower surface of the partitioning plate shown in FIG. 7 and that an O-ring 160 is mounted to the lower surface.

In this modification, when the partitioning plate-driver 265 operates, the partitioning plate 260 closes the front end of the electron optical column 200 via the O-ring 160. Consequently, the inside of the column 200 is hermetically isolated from the inside of the vacuum chamber 230.

In this structure, after the partitioning plate 260 is closed as described above, leaking gas is supplied from the bottom side of the vacuum chamber 230 via the tube 231. In this structure, too, contamination into the electron optical column 200 can be prevented.

Having thus described our invention with the detail and particularity required by the Patent Laws, what is desired protected by Letters Patent is set forth in the following claims.

The invention claimed is:

1. A sample inspection apparatus comprising:
a film having a first surface to hold a sample thereon;
a vacuum chamber for reducing pressure of an ambient in contact with a second surface of the film;
primary beam optical column enclosing the electron gun and objective lens connected with the vacuum chamber via an opening for passage of a primary beam irradiating the sample via the film;
signal detection means for detecting a secondary signal produced from the sample in response to the primary beam irradiation; and a partitioning member located outside of the primary beam optical column capable of partitioning off a region between the film and a front end of the primary beam optical column without hermetically isolating a side on which the film is located from a side on which the front end of the primary beam optical column is located inside the vacuum chamber.

2. A sample inspection apparatus as set forth in claim 1, wherein there is further provided detection means for detecting any damage to the film, and wherein when the detection means has detected the damage to the film, the partitioning member partitions off said region.

3. A sample inspection apparatus as set forth in claim 2, wherein there is further provided pressure restoration means which, when said detection means has detected the damage to the film, returns the inside of the primary beam optical column and the inside of the vacuum chamber to atmospheric pressure.

4. A sample inspection apparatus as set forth in claim 3, wherein when said detection means has detected the damage to the film, said pressure restoration means returns the inside of the primary beam optical column and the inside of the vacuum chamber to atmospheric pressure by supplying gas into the vacuum chamber via the primary beam optical column.

5. A sample inspection apparatus as set forth in any one of claims 2 to 4, wherein said detection means detects the damage to the film based on a rise in pressure inside the vacuum chamber.

6. A sample inspection apparatus as set forth in any one of claims 1 to 4, wherein said partitioning member has a receiver dish structure.

7. A sample inspection apparatus as set forth in any one of claims 1 to 4, wherein said signal detection means is mounted on said partitioning member.

8. A sample inspection apparatus as set forth in any one of claims 1 to 4, wherein said first surface of the film holds the sample in an open state to permit access to the surface from the outside.

9. A sample inspection apparatus as set forth in any one of claims 1 to 4, further comprising:
a manipulator having a front-end portion capable of being brought close to or making contact with the sample held on the first surface of the film; and
optical image acquisition means for observing the sample and the manipulator.

10. A sample inspection apparatus as set forth in any one of claims 1 to 4, wherein the first surface of said film is an upper surface of the film, while the second surface of the film is a lower surface of the film.

11. A sample inspection apparatus as set forth in any one of claims 1 to 4, wherein said primary beam is a beam of charged particles or an electron beam, and wherein said secondary signal is at least one type of secondary electrons, backscattered electrons, X-rays, and cathodoluminescent light.

12. A sample inspection method for inspecting a sample using a sample inspection apparatus as set forth in any one of claims 1 to 4.

13. The sample inspection apparatus according to claim 1, wherein the primary beam optical column encloses a primary beam gun, the primary beam optical column has an orifice at the optical axis thereof; and when in the partitioning position the partitioning member locates well beyond the orifice between the film and the primary beam gun.

14. A sample inspection method comprising the steps of:
holding a sample on a first surface of a film;
reducing pressure of a space in contact with a second surface of the film;
irradiating the sample via the film with a primary beam passed through a primary beam optical column enclosing an electron gun and objective lens connected with the reduced pressure space via an opening for passage of the primary beam;
inspecting the sample by detecting a secondary signal produced from the sample in response to the primary beam irradiation; and
causing a partitioning member located outside of the primary beam optical column to partition off a region between the film and a front end of the primary beam optical column which are disposed opposite to each other, without hermetically isolating a side on which the film is located from a side on which the front end of the primary beam optical column is located inside the space when any damage to the film is detected.

15. A sample inspection method as set forth in claim 14, wherein when any damage to said film is detected, the inside of said primary beam optical column and said space are returned to atmospheric pressure.

16. A sample inspection method as set forth in claim 15, wherein when any damage to said film is detected, the inside of said primary beam optical column and said space are returned to the atmospheric pressure by supplying gas into said space via the inside of the primary beam optical column.

17. A sample inspection method as set forth in any one of claims 14 to 16, wherein the damage to said film is detected based on a rise in pressure inside said space.

18. A sample inspection method as set forth in any one of claims 14 to 16, wherein said partitioning member has a receiver dish structure.

19. A sample inspection method as set forth in any one of claims 14 to 16, wherein said first surface of the film holds the sample in an open state to permit access to the film from the outside.

20. A sample inspection method as set forth in any one of claims 14 to 16, wherein the sample held on the first surface of said film is manipulated, and wherein an optical image of the sample is acquired.

21. A sample inspection method as set forth in any one of claims 14 to 16, wherein the first surface of said film is an upper surface of the film, while the second surface of the film is a lower surface of the film.

22. A sample inspection method as set forth in any one of claims 14 to 16, wherein said primary beam is a beam of charged particles or an electron beam, and wherein said secondary signal is at least one type of secondary electrons, backscattered electrons, X-rays, and cathodoluminescent light.

* * * * *

UNITED STATES PATENT AND TRADEMARK OFFICE
CERTIFICATE OF CORRECTION

| | | |
|---|---|---|
| PATENT NO. | : 8,119,994 B2 | Page 1 of 1 |
| APPLICATION NO. | : 12/407918 | |
| DATED | : February 21, 2012 | |
| INVENTOR(S) | : Hidetoshi Nishiyama et al. | |

It is certified that error appears in the above-identified patent and that said Letters Patent is hereby corrected as shown below:

Column 18, Line 4, Claim 13, delete "thereof;" and insert -- thereof, --

Signed and Sealed this
Twenty-ninth Day of May, 2012

David J. Kappos
*Director of the United States Patent and Trademark Office*